United States Patent
Kocherlakota et al.

(10) Patent No.: US 8,618,146 B2
(45) Date of Patent: Dec. 31, 2013

(54) EPOTHILONE COMPOUND FORMULATIONS

(75) Inventors: Chandrasekhar Kocherlakota, Secunderabad (IN); Tarun Singh, Bijnor (IN); Nagaraju Banda, Hyderabad (IN); Prasad Vure, Secunderabad (IN); Aparna Mulupuru, Hyderabad (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 0 days.

(21) Appl. No.: 13/342,267

(22) Filed: Jan. 3, 2012

(65) Prior Publication Data

US 2012/0277274 A1    Nov. 1, 2012

Related U.S. Application Data

(60) Provisional application No. 61/442,860, filed on Feb. 15, 2011, provisional application No. 61/523,451, filed on Aug. 15, 2011.

(30) Foreign Application Priority Data

Jan. 3, 2011 (IN) ............................... 11/CHE/2011
Jun. 20, 2011 (IN) ........................... 2089/CHE/2011

(51) Int. Cl.
C07D 493/04 (2006.01)
A61P 35/00 (2006.01)
A61K 31/427 (2006.01)

(52) U.S. Cl.
USPC ........................................................ 514/365

(58) Field of Classification Search
USPC ........................................................ 514/365
See application file for complete search history.

(56) References Cited

U.S. PATENT DOCUMENTS

| 5,183,746 | A | 2/1993 | Shaked et al. |
| 6,365,749 | B1 | 4/2002 | Kim et al. |
| 7,022,330 | B2 | 4/2006 | Bandyopadhyay et al. |
| 2009/0069393 | A1* | 3/2009 | Bandyopadhyay et al. .. 514/365 |
| 2010/0311796 | A1* | 12/2010 | Wang et al. .................. 514/365 |

FOREIGN PATENT DOCUMENTS

| WO | 93/10121 A1 | 5/1993 |
| WO | 97/19086 A1 | 5/1997 |
| WO | WO 2009/100571 | * 8/2009 ........... C07D 417/06 |

OTHER PUBLICATIONS

G. Hofle et al., "Epothilone A and B—Novel 16-Membered Macrolides with Cytotoxic Activity: Isolation, Crystal Structure, and Conformation in Solution," Angewandte Chemie International Edition in English, vol. 35, No. 13/14, pp. 1567-1569 (1996).

K. C. Nicolaou, et al., "Designed Epothilones: Combinatorial Synthesis, Tubulin Assembly Properties, and Cytotoxic Action Against Taxol-Resistant Tumor Cells," Angewandte Chemie International Edition in English, vol. 36, No. 19, pp. 2097-2103 (1997).

D-S Su, et al., "Structure-Activity Relationship of the Epothilones and the First In Vivo Comparison with Paclitaxel," Angewandte Chemie International Edition in English, vol. 36, No. 19, pp. 2093-2097 (1997).

N. Ni, et al., "Use of Pure t-Butanol as a Solvent for Freeze-Drying: a Case Study," International Journal of Pharmaceutics, vol. 226, pp. 39-46 (2001).

* cited by examiner

*Primary Examiner* — Jeffrey S. Lundgren
*Assistant Examiner* — Zenab Olabowale
(74) *Attorney, Agent, or Firm* — Pergament Gilman & Cepeda LLP; Milagros A. Cepeda; Edward D. Pergament (57) ABSTRACT

The present application relates to compositions for parenteral administration of epothilone compounds, such as ixabepilone.

14 Claims, 2 Drawing Sheets

EPOTHILONE COMPOUND FORMULATIONS

The present application relates to compositions for parenteral administration of epothilone compounds.

Epothilones are macrolide compounds having utility as pharmaceutical active ingredients. For example, epothilones A and B having the structure below, where R is H for epothilone A and R is $CH_3$ for epothilone B, exert microtubule-stabilizing effects similar to those of paclitaxel (the active ingredient in TAXOL®), and hence have cytotoxic activity against rapidly proliferating cells, such as tumor cells, and are useful for treating hyperproliferative cellular diseases; see G. Hofle et al., "Epothilone A and B—Novel 16-Membered Macrolides with Cytotoxic Activity: Isolation, Crystal Structure, and Conformation in Solution, "*Angewandte Chemie International Edition in English*, Vol. 35, No. 13/14, pages 1567-1569 (1996), and International Application Publication Nos. WO 93/10121 and WO 97/19086.

Derivatives and analogs of epothilones A and B have been synthesized and may be used to treat a variety of cancers and other abnormal proliferative diseases. Such analogs are disclosed in Hofle et al., id., K. C. Nicolaou et al., "Designed Epothilones: Combinatorial Synthesis, Tubulin Assembly Properties, and Cytotoxic Action against Taxol-Resistant Tumor Cells," *Angewandte Chemie International Edition in English*, Vol. 36, No. 19, pages 2097-2103 (1997), and D-S. Su et al., "Structure-Activity Relationship of the Epothilones and the First In Vivo Comparison with Paclitaxel," *Angewandte Chemie International Edition in English*, Vol. 36, No. 19, pages 2093-2097 (1997). Analogs of epothilones that have been found to have advantageous activity are represented by formula I, wherein the various symbols are as described below. While these compounds possess significant therapeutic properties, they also present difficulties to those skilled in the art of pharmaceutical compounding, as a result of certain properties, as will be detailed herein below.

The process of lyophilization is described explicitly in U.S. Pat. No. 5,183,746. U.S. Pat. No. 7,022,330 describes a process of lyophilization of epothilone analogs using a mixture of at least 50% v/v tertiary-butyl alcohol and water.

Tertiary-butyl alcohol is an excellent medium for freeze drying due to its low toxicity, high vapor pressure and low melting point. See N. Ni et al, "Use of Pure t-Butanol as a Solvent for Freeze-Drying: a Case Study," *International Journal of Pharmaceutics*, Vol. 226, pages 39-46 (2001), describing the lyophilization of 1-(2-chloroethyl)-3-sarcosinamide-1-nitrosourea.

The currently marketed IXEMPRA® product contains the active ingredient ixabepilone, a semisynthetic analog of epothilone B having structural formula III and a chemical name (1S,3S,7S,10R,11S,12S,16R)-7,11-dihydroxy-8,8,10,12,16-pentamethyl-3-[(1E)-1-methyl-2-(2-methyl-4-thiazolyl)ethenyl]-17-oxa-4-azabicyclo[14.1.0]heptadecane-5,9-dione. It is available in vials containing 15 or 45 mg of the lyophilized compound. In preparing the product, ixabepilone is initially solubilized with a mixture of tertiary-butyl alcohol and water, and then lyophilized under optimized conditions. The lyophilized drug is reconstituted first with a mixture of a polyethoxylated castor oil surfactant and anhydrous ethanol, and thereafter diluted with Lactated Ringer's Injection to a concentration appropriate for administration.

SUMMARY

Aspects of the application relate to formulations and the preparation thereof for epothilone compounds having formula A, where R is hydrogen, or an alkyl, substituted alkyl, aryl, substituted aryl, or heterocyclic group, including any salts and any stereoisomers of the compounds or salts.

Aspects of the present application relate to formulations and the preparation thereof for epothilone analogs represented by formulas I and II.

wherein the various symbols are as described below.

In one embodiment, the present application relates to formulations and preparations of the epothilone drug (1S,3S,7S, 10R,11S,12S,16R)-7,11-dihydroxy-8,8,10,12,16-pentamethyl-3-[(1E)-1-methyl-2-(2-methyl-4-thiazolyl)ethenyl]-17-oxa-4-azabicyclo[14.1.0]heptadecane-5,9-dione, or ixabepilone.

In embodiments, the application provides compositions of epothilone compounds prepared using processes comprising vacuum drying.

In embodiments, the application provides compositions of epothilone compounds prepared using a mixture of tertiary-butanol and water as a solvent and using processes comprising vacuum drying.

In embodiments the application provides compositions of epothilone compounds prepared using mixtures of tertiary-butanol and other non-aqueous organic solvents as solvents, and using processes comprising vacuum drying.

In embodiments the application provides compositions of epothilone compounds prepared with tertiary-butanol alone as a solvent, and using processes comprising vacuum drying.

In embodiments, the application provides compositions of epothilone compounds prepared using only tertiary-butyl alcohol as a solvent and using processes comprising lyophilization.

In embodiments, the application provides compositions of epothilone compounds, prepared using tertiary-butyl alcohol in combination with other non-aqueous organic solvents that are lyophilisable, and using processes comprising lyophilization.

In embodiments, the application provides compositions of epothilone compounds, prepared using mixtures of acetone and tertiary-butyl alcohol and using processes comprising lyophilization.

In embodiments, the application provides compositions of epothilone compounds, prepared using mixtures of acetonitrile and tertiary-butyl alcohol, and processes of lyophilization.

In embodiments, the application provides reconstitution solvents for the compositions of epothilone compounds comprising a mixture of a surfactant other than a Cremophor™ product and anhydrous alcohol.

In embodiments, the application provides reconstitution solvents for the compositions of epothilone compounds comprising a mixture of a Cremophor™ product and an alcohol that is not dehydrated alcohol.

In embodiments, the present application provides processes for preparing compositions of epothilone compounds having significantly lower amounts of drug-related impurities than the currently marketed IXEMPRA preparation, comprising the use of a mixture of a non-aqueous organic solvent and tertiary-butyl alcohol, and including lyophilization.

In embodiments, the present application provides pharmaceutical formulations of epothilone compounds having significantly lower amounts of total drug-related impurities than the currently marketed IXEMPRA preparation.

In embodiments the present application provides epothilone analogs manufactured in bulk, under sterile conditions, using any of the processes mentioned above.

DETAILED DESCRIPTION

Aspects of the application relate to formulations and the preparation thereof for epothilone compounds having formula A, where R is hydrogen, or an alkyl, substituted alkyl, aryl, substituted aryl, or heterocyclic group, including any salts and any stereoisomers of the compounds or salts.

Aspects of the present application relate to formulations and their preparation for epothilone analogs represented by formula I and II, wherein the various symbols are as described below.

Lyophilized preparations of epothilone analogs are described in U.S. Pat. No. 7,022,330. However, a limitation of this process is that the batch size must necessarily be small to avoid exposure of the epothilone to aqueous media for prolonged times. One way to overcome this problem is to use pure tertiary-butyl alcohol or mixtures of tertiary-butyl alcohol and any other lyophilizable organic solvent as the solvent for lyophilization. This would enable the manufacture of larger batch sizes thereby saving resources and reducing costs. To avoid the degradation of the compounds represented by Formulas I and II, a suitable non-aqueous organic solvent system is tertiary-butyl alcohol (TBA). Another solvent system found to be particularly advantageous in terms of stability of the finished dosage form is a mixture of tertiary-butyl alcohol and acetone. Both the processes of forming the solution and subsequent lyophilization are to be carried out in vessels such that the epothilone analogs are protected from exposure to light.

In embodiments, the application provides compositions of epothilone compounds prepared using processes comprising vacuum drying.

In embodiments the application provides compositions of epothilone compounds prepared using a mixture of tertiary-butanol and water as a solvent, and using processes comprising vacuum drying.

In embodiments the application provides compositions of epothilone compounds prepared using mixtures of tertiary-butanol and other non-aqueous organic solvents as solvents, and using processes comprising vacuum drying.

In embodiments the application provides compositions of epothilone compounds prepared tertiary-butanol alone as a solvent, and using processes comprising vacuum drying.

In embodiments, the application provides compositions of epothilone compounds prepared using only tertiary-butyl alcohol and processes of lyophilization.

In embodiments, the application provides compositions of epothilone compounds prepared using tertiary-butyl alcohol in combination with other non-aqueous organic solvents that are lyophilisable, and processes of lyophilization.

In embodiments, the application provides compositions of epothilone compounds, prepared using mixtures of acetone and tertiary-butyl alcohol, and processes of lyophilization.

In embodiments, the application provides compositions of epothilone compounds, prepared using mixtures of acetonitrile and tertiary-butyl alcohol, and processes of lyophilization.

In embodiments, the present application provides processes for the preparation of compositions of epothilone compounds having significantly lower amounts of drug-related impurities than the marketed IXEMPRA preparation, involving the use of mixtures of non-aqueous organic solvents and tertiary-butyl alcohol, and processes of lyophilization In embodiments, the present application provides pharmaceutical formulations of epothilone compounds having significantly lower amounts of total drug-related impurities, as compared to the currently marketed IXEMPRA preparation.

In embodiments of the present application, an epothilone compound is initially dissolved in a mixture of tertiary-butyl alcohol and an organic solvent and the solution is lyophilized. The lyophilized drug is reconstituted, first with a mixture of a surfactant, other than a Cremophor™ product, and anhydrous ethanol, and thereafter is diluted with Lactated Ringer's Injection to a concentration appropriate for administration.

In embodiments of the present application, an epothilone compound is initially dissolved in a mixture of tertiary-butyl alcohol and water, and then subjected to vacuum drying. The dried drug is reconstituted, first with a mixture of a polyethoxylated castor oil surfactant and anhydrous ethanol, and thereafter diluted with Lactated Ringer's Injection to a concentration appropriate for administration.

In embodiments of the present application, an epothilone compound is initially dissolved in a mixture of tertiary-butyl alcohol and water, and then subjected to vacuum drying. The product thus obtained is reconstituted with a mixture of a surfactant, other than a Cremophor™ product, and anhydrous ethanol, and thereafter diluted with Lactated Ringer's Injection to a concentration appropriate for administration.

In embodiments of the present application, an epothilone compound is initially dissolved in a mixture of tertiary-butyl alcohol and an organic solvent and then is lyophilized. The lyophilized drug is reconstituted, first with a mixture of a polyethoxylated castor oil surfactant and anhydrous ethanol, and thereafter diluted with Lactated Ringer's Injection to a concentration appropriate for administration.

In embodiments of the present application, an epothilone compound is initially dissolved in tertiary-butyl alcohol alone, and then lyophilized. The lyophilized drug is reconstituted, first with a mixture of a polyethoxylated castor oil surfactant and anhydrous ethanol, and thereafter diluted with Lactated Ringer's Injection to a concentration appropriate for administration.

In embodiments of the present application, an epothilone compound is initially dissolved in tertiary-butyl alcohol alone, and then lyophilized. The lyophilized drug is reconstituted, first with a mixture of a surfactant, other than a Cremophor™ product, and anhydrous ethanol, and thereafter diluted with Lactated Ringer's Injection to a concentration appropriate for administration.

In embodiments of the present application, an epothilone compound is initially dissolved in a mixture of tertiary-butyl alcohol and water, and then lyophilized. The lyophilized drug is reconstituted, first with a mixture of a polyethoxylated castor oil surfactant and an alcohol that is not dehydrated alcohol, and thereafter diluted with Lactated Ringer's Injection to a concentration appropriate for administration.

In embodiments of the present application, an epothilone compound is initially dissolved in a mixture of tertiary-butyl alcohol and water, and then lyophilized. The lyophilized drug is reconstituted, first with a mixture of a surfactant other than a Cremophor™ product, and an alcohol that is not dehydrated alcohol, and thereafter diluted with Lactated Ringer's Injection to a concentration appropriate for administration.

In embodiments of the present application, an epothilone compound is initially dissolved in a mixture of tertiary-butyl alcohol and water, and then lyophilized. The lyophilized drug is reconstituted, first with a mixture of a polyethylene glycol and alcohol that is not dehydrated alcohol, and thereafter diluted with Lactated Ringer's Injection to a concentration appropriate for administration.

In embodiments of the present application, an epothilone compound is initially dissolved in a mixture of tertiary-butyl alcohol and an organic solvent, and then subjected to vacuum drying. The dried drug is reconstituted, first with a mixture of a polyethoxylated castor oil surfactant and anhydrous ethanol, and thereafter diluted with Lactated Ringer's Injection to a concentration appropriate for administration.

In embodiments of the present application, an epothilone compound is initially dissolved in a mixture of tertiary-butyl alcohol and an organic solvent, and then subjected to vacuum drying. The dried drug is reconstituted, first with a mixture of a surfactant, other than a Cremophor™ product, and anhydrous ethanol, and thereafter diluted with Lactated Ringer's Injection to a concentration appropriate for administration.

In embodiments of the present application, an epothilone compound is initially dissolved in tertiary-butyl alcohol alone, and then subjected to vacuum drying. The dried drug is reconstituted, first with a mixture of a polyethoxylated castor oil surfactant and anhydrous ethanol, and thereafter diluted with Lactated Ringer's Injection to a concentration appropriate for administration.

In embodiments of the present application, an epothilone compound is initially dissolved in tertiary-butyl alcohol alone, and then subjected to vacuum drying. The dried drug is reconstituted, first with a mixture of a surfactant other than a Cremophor™ product, and anhydrous ethanol, and thereafter diluted with Lactated Ringer's Injection to a concentration appropriate for administration.

An aspect of the present application involves crystallization of the drug, drying the crystals, and filling the dried powder into vials, all under sterile conditions.

In an aspect of the present application, an epothilone formulation can be manufactured in bulk, under sterile conditions, using any of the processes mentioned above.

An aspect of the present application provides alternative formulations for the administration of epothilone or epothilone analoas represented by formula I.

I

As used in formula I and throughout the specification, Q is

M is oxygen, sulfur, $NR^8$, or $CR^9R^{10}$;

$R^6$ is hydrogen, or an alkyl, substituted alkyl, aryl, substituted aryl, cycloalkyl, heterocyclic, or substituted heterocyclic group;

$R^8$ is hydrogen, or an alkyl, substituted alkyl, $R^{11}$(C=O)—, $R^{12}$O(C=O)—, or $R^{13}SO_2$ group; and $R^9$ and $R^{10}$ are each independently hydrogen, halogen, or an alkyl, substituted alkyl, aryl, heterocyclo, hydroxy, $R^{14}$(C=O)—, or $R^{15}$(C=O)— group; and $R^1$, $R^2$, $R^3$, $R^4$, $R^5$, $R^7$, $R^{11}$, $R^{12}$, $R^{13}$, $R^{14}$, and $R^{15}$ are each independently hydrogen, or an alkyl, substituted alkyl, aryl, substituted aryl, or heterocyclic group, and when $R^1$ and $R^2$ are each alkyl they, together with the carbon atom to which they are attached, can be joined to form a cycloalkyl group.

Examples of non-ionic surfactants that can be used include, but are not limited to, fatty alcohols such as cetyl, stearyl, cetostearyl, and oleyl alcohols, glyceryl glycols, laurate, polysorbates, sorbitan fatty acid esters, macrogol-glycerol fatty acid esters (e.g., Cremophor™ products), poloxamers, non-ionic phospholipids, etc. In embodiments, a nonionic surfactant is one of the polysorbates Tween™ 60 or Tween™ 80, one of the sorbitan fatty acid esters such as Span™ 80, or a polyethylene glycol. The commercial product Cremophor™ ELP, a polyethoxylated castor oil, and the purified Cremophor™ ELP, are formed by reacting about 35 moles of ethylene oxide with a mole of castor oil.

In embodiments, the epothilone analog within those represented by formula I is (1S,3S,7S,10R,11S,12S,16R)-7,11-dihydroxy-8,8,10,12,16-pentamethyl-3-[(1E)-1-methyl-2-(2-methyl-4-thiazolyl)ethenyl]17-oxa-4-azabicyclo[14.1.0]heptadecane-5,9-dione represented by formula III.

III

The compounds represented by formulas I and III above and their preparation are described in U.S. Pat. No. 6,365,749 B1, the disclosure of which is incorporated herein by reference. The compounds represented by formulas I and III above may exist as multiple optical, geometric, and stereoisomers. While the compounds shown herein are depicted for one optical orientation, the present application includes the use of all isomers and mixtures thereof.

The compounds represented by formulas A, I, and III, particularly the latter, present difficulties from the viewpoint of compounding suitable formulations for administration, in that they possess very low solubility in aqueous media, rapidly degrade in contact with aqueous media, are sensitive to low pH when in solution, are light sensitive, are "Class D" cytotoxic, and have exceptionally poor wetting characteristics. Any one or two of these properties might be compensated for in compounding a pharmaceutical formulation for intravenous administration, but the combination of all of them presents a formidable challenge to the pharmaceutical compounding chemist. Given the constraint that materials to be utilized in compounding an intravenous formulation must be approved for intravenous administration, the formulation provided in accordance with the present application unexpectedly was found to be suitable for overcoming the disadvantageous properties of the subject epothilone analogs as noted above. Because of the fact that the subject epothilone analogs are poorly soluble in aqueous media and, in fact, rapidly degrade in contact therewith, they frequently are formulated in lyophilized form.

To avoid the degradation of the compounds represented by Formulas A, I, and III, a suitable non-aqueous organic solvent system comprises tertiary-butyl alcohol (TBA). TBA is an excellent medium for freeze drying due to its low toxicity, high vapor pressure and low melting point. See N. Ni et al, id. A solution of the epothilone compound in pure TBA or other lyophilisable solvents, except water, or mixtures thereof is subjected to lyophilization. Both the process of forming the solution and subsequent lyophilization can be carried out in vessels such that the epothilone compounds are protected against exposure to light.

The present application utilizes processes of lyophilization for epothilone compositions using a mixture of at least tertiary-butyl alcohol and water, or tertiary-butyl alcohol alone, or organic solvents alone, or mixtures of tertiary-butyl alcohol with organic solvents.

A primary drying stage of lyophilization of solutions formed as described above is carried out at temperatures from about 40° C. to about −80° C. In embodiments, the lyophilization is carried out at temperatures about −10° C. under high vacuum, i.e., from about 5 millitorr to about 500 millitorr. In embodiments, the applied vacuum is about 200 millitorr. In embodiments the lyophilization cycle is for an extended period, i.e., from about 8 hours to about 120 hours. In embodiments, the period is about 100 hours. Lyophilization in this temperature range produces an amorphous product that is desirable for an intravenous preparation.

Residual solvents in a lyophilized product can be removed by a secondary drying stage that is carried out at comparatively low temperatures, i.e., from about 10° C. to about 30° C. In embodiments, the residual solvents are removed at about 25° C. under high vacuum, i.e., from about 5 millitorr to about 30 millitorr. In embodiments, the vacuum is about 10 millitorr.

An example of a useful lyophilization procedure comprises:

a) dissolving an epothilone compound in a solvent;
b) cooling the solution to 2° C. to about 8° C.;
c) freezing the solution for about 2 to about 10 hours at a temperature ranging from about −50° C. to about 10° C.;
d) drying the frozen solution for about 48 to about 120 hours;
e) increasing the temperature at rates from about 3° C./hour to about 12° C./hour, to a temperature range from about −60° C. to about +15° C.;
f) holding at the temperature range of step e) for from about 24 to about 48 hours;
f) increasing the temperature at about 3° C./hour to about 12° C./hour to a temperature range from about +10° C. to about +30° C.; and
g) holding at the temperature range of step f) for at least 24 hours.

An aspect of the present application includes preparing formulations of the compounds represented by formulas A, I, and III using a process of vacuum drying. A suitable organic co-solvent system such as pure TBA, another organic solvent, or mixtures thereof may be used to form a solution of the epothilone compounds. The solution is then subjected to drying in a vacuum dryer. The solution may also be dried using any of a number of methods such as thin film drying, spray drying, lyophilization without freezing, or placing in an oven. The resulting dry powder can be reconstituted for use with a mixture of equal parts by volume of Dehydrated Alcohol USP and a nonionic surfactant. The dry powder and vehicle for reconstitution are packaged separately in appropriate vials. The final dilution of the reconstituted epothilone compound in the formulations of the application may be carried out with a suitable parenteral diluent such as Lactated Ringer's Injection.

In embodiments, vacuum drying of solutions of epothilone compounds is carried out at temperatures at which the solution does not freeze (e.g., above about −30° C.), under a gradually applied vacuum, i.e., from about 0.05 millibarr to about 600 millibarr, for sufficient period of times to obtain a powder residue. Subsequently, the vacuum is reduced to about 50 millitorr to about 300 millitorr. In embodiments, the vacuum is about 200 millitorr, and is held for a sufficient time to substantially remove residual solvent.

Alternatively, an epothilone compound can be lyophilized or dried from dispersions. A stock solution containing the drug can be prepared in a suitable solvent, i.e., one that can dissolve the drug from 0.5 to more than 40 mg/mL. A sufficient quantity of this stock solution may be added to a suitable amount of Water for Injection USP and the resulting suspension may be subjected to lyophilization or vacuum drying as described above.

An aspect of the present application includes the manufacture of lyophilized or vacuum dried drug in bulk. This can be achieved by the processes described above with suitable modifications in process conditions. Alternatively, the processing of the epothilone compound may be carried out under aseptic conditions and the sterile drug thus obtained may be directly filled into vials and sealed.

Formulations of embodiments of the present application have been tested for their storage stability under stress conditions, such as using the accelerated stability testing conditions of 40° C. and 75% relative humidity (RH), and at 60° C. It has been found that a lyophilized formulation of epothilone compounds according the present application, wherein the solvent is a mixture of tertiary-butyl alcohol and acetone or a mixture of tertiary-butyl alcohol and acetonitrile, is more stable against drug-related impurity formation than the currently marketed IXEMPRA preparation.

Impurities in epothilone formulations, and the drug content, can be determined using well known analytical procedures such as high performance liquid chromatography (HPLC). For example, a sample of a formulation is dissolved in acetonitrile and injected into a ACE C18 150×4.6 mm column and run for about 90 minutes using a mixture of acetate buffer and acetonitrile as the mobile phase. The percentage of any impurity is calculated by comparing the areas under the peaks.

The lyophilized/vacuum dried epothilone analog compositions can be reconstituted with a mixture of equal parts by volume of Dehydrated Alcohol, USP and a nonionic surfactant, or mixtures of Alcohol USP and a nonionic surfactant. The lyophilized product and vehicle for reconstitution can be packaged separately in appropriate vials. To minimize the amount of surfactant in the reconstituted solution, only a sufficient amount of the vehicle is provided to form a solution having a concentration from about 2 mg/mL to about 4 mg/mL of the epothilone compound. Once dissolution of the drug is achieved, the solution is further diluted prior to use with a suitable parenteral diluent. Such diluents are well known to those of ordinary skill in the art. These diluents are generally available in clinical facilities. It is, however, within the scope of the present application to package the subject epothilone compounds with a third vial containing sufficient parenteral diluent to prepare the final concentration for administration. In embodiments, the diluent is Lactated Ringer's Injection. The final concentration for administration would, in embodiments, contain from about 0.1 mg/mL to about 0.9 mg/mL of the epothilone compound.

The final dilution of the reconstituted epothilone compound in a formulation of the application may be carried out with preparations that are useful for infusion, for example, 5% Dextrose Injection, Lactated Ringer's and Dextrose Injection, Sterile Water for Injection, and the like. In embodiments, because of its narrow pH range, pH 6.0 to 7.5, Lactated Ringer's Injection is used. Each 100 mL of Lactated Ringer's Injection contains 0.6 g of sodium chloride, 0.31 g of sodium lactate, 0.03 g of potassium chloride, and 0.02 g of calcium chloride•$2H_2O$. The osmolarity is 275 mOsm/L, which is very close to isotonicity.

Reconstituted preparations according to the present application, i.e., a solution of the epothilone compoundg in an alcohol-surfactant vehicle, can be stored for up to about 24 hours before being further diluted for administration. The final dilution can be administered by intravenous infusion, typically over a period of up to an hour.

DEFINITIONS

The following commercially available products mentioned herein have the following compositions: Cremophor™ ELP is a grade of a nonionic solubilizer and emulsifier made by reacting castor oil with ethylene oxide in a molar ratio of 1:35. Cremophor™ is a registered trademark of BASF Corp. Solutol® is a 12-hydroxystearic acid-polyethylene glycol copolymer. Solutol® is a registered trademark of BASF Aktiengesellschaft. Tween™ 60 and Tween™ 80 are nonionic surfactants and emulsifiers derived from polyoxyethylated sorbitan and oleic acid. Tween™ is a registered trademark of ICI Americas, Inc.

The following definitions are used in connection with the compounds of the present application unless the context indicates otherwise. The term "alkyl" refers to optionally substituted straight- or branched-chain saturated hydrocarbon groups having from 1 to 20 carbon atoms. In embodiments, alkyl groups have from 1 to 7 carbon atoms. The expression "lower alkyl" refers to optionally substituted alkyl groups having from 1 to 4 carbon atoms.

The term "substituted alkyl" refers to an alkyl group substituted by, for example, from one to four substituents, such as, halo, trifluoromethyl, trifluoromethoxy, hydroxy, alkoxy, cycloalkyoxy, heterocylooxy, oxo, alkanoyl, aryl, aryloxy, aralkyl, alkanoyloxy, amino, alkylamino, arylamino, aralkylamino, cycloalkylamino, heterocycloamino, disubstituted amino in which the two substituents on the amino group are selected from alkyl, aryl, aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g., $SO_2NH_2$), substituted sulfonamido, nitro, cyano, carboxy, carbamyl (e.g., $CONH_2$), substituted carbamyl (e.g., CONH alkyl, CONH aryl, CONH aralkyl or instances where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl or the like. Wherein, as noted above, the substituents themselves are further substituted, such further substituents are selected from the group consisting of halogen, alkyl, alkoxy, aryl and aralkyl. The definitions given herein for alkyl and substituted alkyl also apply to the alkyl portion of the alkoxy groups as well.

The term "halogen" or "halo" refers to fluorine, chlorine, bromine, and iodine.

The term "ring system" refers to an optionally substituted ring system containing one to three rings and at least one carbon to carbon double bond in at least one ring. Exemplary ring systems include, but are not limited to, an aryl or a partially or fully unsaturated heterocyclic ring system, which may be optionally substituted.

The term "aryl" refers to monocyclic or bicyclic aromatic hydrocarbon groups having from 6 to 12 carbon atoms in the ring portion, for example, phenyl, naphthyl, biphenyl, and diphenyl groups, each of which may be substituted.

The term "aralkyl" refers to an aryl group bonded to a larger entity through an alkyl group, for example, a benzyl group.

The term "substituted aryl" refers to an aryl group substituted by, for example, one to four substituents such as alkyl, substituted alkyl, halo, trifluoromethyl, trifluoromethoxy, hydroxy, alkoxy, cycloalkyloxy, heterocyclooxy, alkanoyl, alkanoyloxy, amino, alkylamino, dialkylamino, aralkylamino, cycloalkylamino, heterocycloamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy, and the like. The substituent may be further substituted by one or more members such as halo, hydroxy, alkyl, alkoxy, aryl, substituted alkyl, substituted aryl, and aralkyl.

The term "cycloalkyl" refers to optionally substituted saturated cyclic hydrocarbon ring systems, in one embodiment containing 1 to 3 rings and 3 to 7 carbons per ring, which may be further fused with an unsaturated $C_3$-$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more of the groups described above as substituents for alkyl groups.

The terms "heterocycle," "heterocyclic," and "heterocyclo" refer to an optionally substituted, unsaturated, partially saturated, or fully saturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2, or 3 heteroatoms that independently are nitrogen atoms, oxygen atoms, or sulfur atoms, where the nitrogen and sulfur heteroatoms may also optionally be oxidized or the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromanyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents for the terms "ring system," "heterocycle," "heterocyclic," and "heterocyclo" include one or more substituent groups as described above for substituted alkyl or substituted aryl, and smaller heterocyclo groups, such as, epoxides, aziridines, and the like.

The term "alkanoyl" refers to —C(O)-alkyl.

The term "substituted alkanoyl" refers to —C(O)-substituted alkyl.

The term "heteroatoms" include oxygen, sulfur, and nitrogen.

The term "organic solvent" refers to any organic solvent that can be evaporated under lyophilization conditions. Certain non-limiting examples of such solvents include: ethanol, 1-propanol, 2-propanol, 1-butanol, ethyl acetate, acetonitrile, dichloromethane, acetone, pentanol, methyl acetate, methanol, carbon tetrachloride, dimethylsulfoxide, chlorobutanol, cyclohexane, dimethylsulfone, acetic acid, methyl ethyl ketone, methyl isobutyl ketone, etc., and any mixtures of two or more thereof.

The term "alcohol" refers to ethyl alcohol containing not more than 96% by volume of ethanol (e.g., Alcohol USP).

As used herein, the terms "composition" and "formulation" refer to the preparation of an epothilone compound in a form suitable for administration to a human. Often, a formulation of the epothilone compound will be administered after addition of at least one pharmaceutically acceptable excipient.

Certain specific aspects and embodiments will be further described by the following examples, being provided only for purposes of illustration and not to be construed as limiting the scope of the disclosure.

EXAMPLE 1

Ixabepilone is dissolved in a mixture of tertiary-butyl alcohol and acetone having a volume ratio of about 1:1, under protection from light. Portions of the solution containing about 15 mg or 45 mg of ixabepilone are filled into depyrogenated glass vials, and then the vials are loosely covered with sterile bromobutyl stoppers and lyophilized under light protected conditions. The resultant lyophilized product (lyophile) is then dried at 25° C. under high vacuum for at least 9 hours. No detectable degradation of the drug is observed during these procedures. The vials are then sealed and labeled.

The lyophile can be reconstituted with 5.5 mL of a 1:1 by volume mixture of alcohol (97% v/v) and Cremophor™ ELP, which typically will be supplied with the drug in a separate vial, to achieve a final drug concentration of 2 mg/mL. Once dissolution is obtained by gently swirling the vial, the solution is diluted to achieve a final concentration of 0.2 mg/mL drug by the addition of 9 mL of Lactated Ringer's for Injection, for each mL of reconstituted drug product.

EXAMPLE 2

The lyophilized product of Example 1 and the currently marketed product IXEMPRA are tested for stability under stress storage conditions. Vials containing 45 mg of drug are stored and samples are analyzed for impurities before and after storage, using a HPLC method. In the tables below, the impurity concentrations are percentages of the label drug content.

TABLE 1

Example 1 - 40° C. and 75% RH Storage

| Impurity | Time | | |
| --- | --- | --- | --- |
| | Initial | 24 Hours | 48 Hours |
| Unidentified Impurity at RRT 0.60 | 0.03 | 0.07 | 0.10 |
| Unidentified Impurity at RRT 0.86 | 0.06 | 0.07 | 0.07 |
| Unidentified Impurity at RRT 1.36 | 0.16 | 0.15 | 0.17 |
| Total Impurities | 0.35 | 0.39 | 0.48 |

TABLE 2

IXEMPRA - 40° C. and 75% RH Storage

| Impurity | Time | |
| --- | --- | --- |
| | Initial | 24 Hours |
| Unidentified Impurity at RRT 0.60 | 0.38 | 0.43 |
| Unidentified Impurity at RRT 0.80 | ND | 0.13 |
| Unidentified Impurity at RRT 0.86 | 0.09 | 0.1 |
| Unidentified Impurity at RRT 1.21 | 0.05 | 0.07 |
| Total Impurities | 0.57 | 0.91 |

As can be seen from Tables 1 and 2, the Example 1 product contains significantly less impurities, both initially and after subjecting it to stress conditions. The total impurities in the Example 1 product are significantly lower after 48 hours at 40° C. and 75% RH, as compared to total impurities in the IXEMPRA product after 24 hours under the same conditions.

TABLE 3

Example 1 - 60° C. Storage

| Impurity | Time | |
| --- | --- | --- |
| | Initial | 24 Hours |
| Unidentified Impurity at RRT 0.60 | 0.03 | 0.25 |
| Unidentified Impurity at RRT 0.86 | 0.06 | 0.07 |
| Unidentified Impurity at RRT 1.36 | 0.16 | 0.15 |
| Total Impurities | 0.35 | 0.55 |

TABLE 4

IXEMPRA - 60° C. Storage

| | Time | |
|---|---|---|
| Impurity | Initial | 24 Hours |
| Unidentified Impurity at RRT 0.60 | 0.38 | 0.53 |
| Unidentified Impurity at RRT 0.80 | ND | 0.12 |
| Unidentified Impurity at RRT 0.86 | 0.09 | 0.09 |
| Unidentified Impurity at RRT 1.21 | 0.05 | 0.04 |
| Total Impurities | 0.57 | 0.93 |

As can be seen from Tables 3 and 4, The Example 1 composition prepared by lyophilising a solution of ixabepilone in a mixture of tertiary-butanol and acetone has significantly lower impurity content than the IXEMPRA product, both initially and after storage at 60° C. for 24 hours.

EXAMPLE 3

Ixabepilone is dissolved in a mixture of tertiary-butyl alcohol and acetonitrile in a volume ratio of about 1:1 under protection from light. Amounts of the solution containing about 15 mg or 45 mg of ixabepilone are filled into depyrogenated glass vials, and then the vials are loosely covered with sterile bromobutyl stoppers and lyophilized under light protected conditions. The lyophilized product (lyophile) is then dried at 25° C. under high vacuum for at least 9 hours. No detectable degradation of the drug is observed during these procedures. The vials are then sealed and labeled.

The lyophile is reconstituted with 5.5 mL of a 1:1 by volume mixture of alcohol (97% v/v) and Cremophor™ ELP, which typically will be supplied with the drug in a separate vial, to achieve a final drug concentration of 2 mg/mL. Once dissolution is obtained by gently swirling the vial, the solution is diluted to achieve a concentration of 0.2 mg/mL by the addition of 9 mL of Lactated Ringer's for Injection for each mL of reconstituted drug product.

EXAMPLE 4

The lyophilized product of Example 3 and the currently marketed product IXEMPRA are tested for stability under stress storage conditions. Vials containing 45 mg of drug are stored and samples are analyzed for impurities before and after storage, using a HPLC method. In the tables below, the impurity concentrations are percentages of the label drug content.

TABLE 5

Example 3 - 40° C. and 75% RH Storage

| | Time | | |
|---|---|---|---|
| Impurity | Initial | 24 Hours | 1 Week |
| Unidentified Impurity at RRT 0.60 | 0.05 | 0.08 | 0.45 |
| Unidentified Impurity at RRT 0.86 | 0.07 | 0.08 | 0.07 |
| Unidentified Impurity at RRT 1.36 | 0.14 | 0.15 | 0.15 |
| Total Impurities | 0.43 | 0.42 | 0.78 |

TABLE 6

IXEMPRA - 40° C. and 75% RH Storage

| | Time | |
|---|---|---|
| Impurity | Initial | 24 Hours |
| Unidentified Impurity at RRT 0.60 | 0.38 | 0.43 |
| Unidentified Impurity at RRT 0.80 | ND | 0.13 |
| Unidentified Impurity at RRT 0.86 | 0.09 | 0.1 |
| Unidentified Impurity at RRT 1.21 | 0.05 | 0.07 |
| Total Impurities | 0.57 | 0.91 |

As can be seen from Tables 5 and 6, the Example 3 product contains significantly less impurities, both initially and after subjecting it to stress conditions. The total impurities in the Example 3 product are significantly lower even after 1 week at 40° C. and 75% RH, as compared to total impurities in the IXEMPRA product after 24 hours under the same conditions.

EXAMPLE 5

Ixabepilone is dissolved in a mixture of tertiary-butyl alcohol and acetonitrile in a volume ratio of about 1:4 under protection from light. Amounts of the solution containing about 15 mg or 45 mg of ixabepilone are filled into depyrogenated glass vials, and then the vials are loosely covered with sterile bromobutyl stoppers and lyophilized under light protected conditions. The lyophilized product (lyophile) is then dried at 25° C. under high vacuum for at least 9 hours. No detectable degradation of the drug is observed during these procedures. The vials are then sealed and labeled.

The lyophile is reconstituted with 5.5 mL of a 1:1 by volume mixture of alcohol (97% v/v) and Cremophor™ ELP, which typically will be supplied with the drug in a separate vial, to achieve a final drug concentration of 2 mg/mL. Once dissolution is obtained by gently swirling the vial, the solution is diluted to achieve a concentration of 0.2 mg/mL by the addition of 9 mL of Lactated Ringer's for Injection for each mL of reconstituted drug product.

EXAMPLE 6

The lyophilized product of Example 5 and the currently marketed product IXEMPRA are tested for stability under stress storage conditions. Vials containing 45 mg of drug are stored and samples are analyzed for impurities before and after storage, using a HPLC method. In the tables below, the impurity concentrations are percentages of the label drug content.

TABLE 7

Example 5 - 40° C. and 75% RH Storage

| | Time | |
|---|---|---|
| Impurity | Initial | 1 week |
| Unidentified Impurity at RRT 0.60 | 0.078 | 0.035 |
| Unidentified Impurity at RRT 0.86 | 0.047 | 0.06 |
| Unidentified Impurity at RRT 1.36 | 0.081 | 0.07 |
| Total Impurities | 0.271 | 0.493 |

TABLE 8

IXEMPRA - 40° C. and 75% RH Storage

| Impurity | Time | |
|---|---|---|
| | Initial | 24 Hours |
| Unidentified Impurity at RRT 0.60 | 0.38 | 0.43 |
| Unidentified Impurity at RRT 0.80 | ND | 0.13 |
| Unidentified Impurity at RRT 0.86 | 0.09 | 0.1 |
| Unidentified Impurity at RRT 1.21 | 0.05 | 0.07 |
| Total Impurities | 0.57 | 0.91 |

As can be seen from Tables 7 and 8, the Example 5 product contains significantly less impurities, both initially and after subjecting it to stress conditions. The total impurities in the Example 5 product are significantly lower even after 1 week at 40° C. and 75% RH, as compared to total impurities in the IXEMPRA product after 24 hours under the same conditions.

TABLE 9

Example 5 - 60° C. Storage

| Impurity | Time | | |
|---|---|---|---|
| | Initial | 24 Hours | 1 Week |
| Unidentified Impurity at RRT 0.60 | 0.078 | 0.317 | 0.503 |
| Unidentified Impurity at RRT 0.86 | 0.047 | 0.052 | 0.061 |
| Unidentified Impurity at RRT 1.36 | 0.081 | 0.086 | 0.076 |
| Total Impurities | 0.271 | 0.498 | 0.876 |

TABLE 10

IXEMPRA - 60° C. Storage

| Impurity | Time | |
|---|---|---|
| | Initial | 24 Hours |
| Unidentified Impurity at RRT 0.60 | 0.38 | 0.53 |
| Unidentified Impurity at RRT 0.80 | ND | 0.12 |
| Unidentified Impurity at RRT 0.86 | 0.09 | 0.09 |
| Unidentified Impurity at RRT 1.21 | 0.05 | 0.04 |
| Total Impurities | 0.57 | 0.93 |

As can be seen from Tables 9 and 10, The Example 5 composition prepared by lyophilising a solution of ixabepilone in a mixture of tertiary-butanol and acetonitrile has lower impurity content than the IXEMPRA product, even after 1 week at 60° C., as compared to total impurities in the IXEMPRA product after 24 hours under the same conditions.

EXAMPLE 7

Ixabepilone is dissolved in a mixture of tertiary-butyl alcohol and methanol in a volume ratio about 2:1 under protection from light. Amounts of the solution containing about 15 mg or 45 mg of ixabepilone are filled into depyrogenated glass vials, and then the vials are loosely covered with sterile bromobutyl stoppers and lyophilized under light protected conditions. The lyophilized product (lyophile) is then dried at 25° C. under high vacuum for at least 9 hours. No detectable degradation of the drug is observed during these procedures. The vials are then sealed and labeled.

The lyophile is reconstituted with 5.5 mL of a 1:1 by volume mixture of Dehydrated Alcohol USP and Cremophor™ ELP, which typically will be supplied with the drug in a separate vial, to achieve a final drug concentration of 2 mg/mL. Once dissolution is obtained by gently swirling the vial, the solution is diluted to achieve a concentration of 0.2 mg/mL by the addition of 9 mL of Lactated Ringer's for Injection for each mL of reconstituted drug product.

EXAMPLE 8

Ixabepilone (9.86 g) is dissolved in tertiary-butanol under protection from light. The solution is promptly lyophilized using under light protected conditions. The resultant lyophilized product (lyophile) is then further dried at 25° C. under high vacuum for not less than 10 hours. No detectable degradation of the drug is observed during these procedures. The lyophile is packaged under sterile conditions into 30 mL vials, each containing 10 mg of drug and a slight excess to allow for vial, needle, and syringe losses.

The lyophile is reconstituted with 5.5 mL of a 1:1 by volume mixture of Dehydrated Alcohol USP and any of Tween 80, Tween 60, polyethylene glycol, or Solutol, which typically will be supplied with the drug in a separate vial, to achieve a final drug concentration of 2 mg/mL. Once dissolution is obtained by gently swirling the vial, the resultant solution is diluted to achieve a concentration of 0.2 mg/mL by the addition of 9 mL of Lactated Ringer's for Injection for each milliliter of constituted drug product.

EXAMPLE 9

Ixabepilone (9.86 g) is dissolved in tertiary-butanol under light protected conditions. The solution is filled into vials, which are then loaded into the shelves of a vacuum dryer. Maintaining a shelf temperature above −30° C., a vacuum of about 300 millitorr is applied gradually and held for sufficient time until a powder residue is obtained from the solution. Subsequently, the vacuum is reduced to about 200 millitorr and held until residual solvent is removed.

The dried product is packaged under sterile conditions into 30 mL vials, each containing 10 mg of drug and a slight excess to allow for vial, needle, and syringe losses.

The dried drug product is reconstituted with 5.5 mL of a 1:1 by volume mixture of Alcohol USP and Cremophor EL., which typically will be supplied with the drug in a separate vial, to achieve a final drug concentration of 2 mg/mL. Once dissolution is obtained by gently swirling the vial, the resultant solution is diluted to achieve a concentration of 0.2 mg/mL by the addition of 9 mL of Lactated Ringer's for Injection for each milliliter of constituted drug product.

EXAMPLE 10

Ixabepilone is dissolved in a mixture of tertiary-butyl alcohol and acetonitrile in a volume ratio about 1:1 under protection from light. The solution is cooled to 2-8° C. and stirred. The solution is filtered through a 0.22 μm filter and amounts of the solution containing about 15 mg or 45 mg of ixabepilone are filled into depyrogenated glass vials which are loosely covered with sterile bromobutyl stoppers and lyophilized under light protected conditions. The lyophilized product (lyophile) is then dried at 25° C. under high vacuum for at least 12 hours. No detectable degradation of the drug is observed during these procedures. The above procedure is carried out under sterile conditions.

Figure 1:
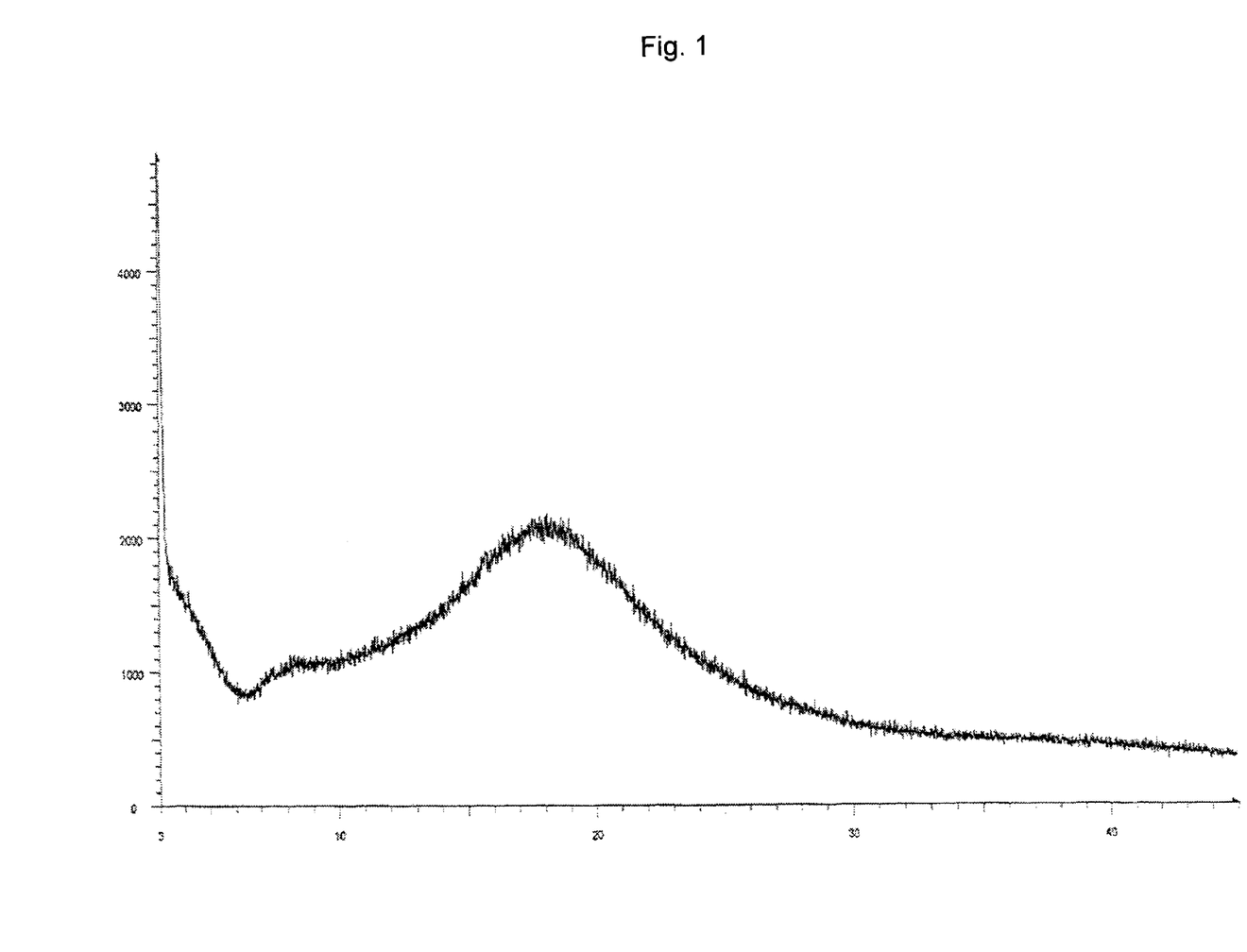
FIG. 1 is an X-ray powder diffraction (XRPD) pattern of a product prepared according to Example 10.
Figure 2:
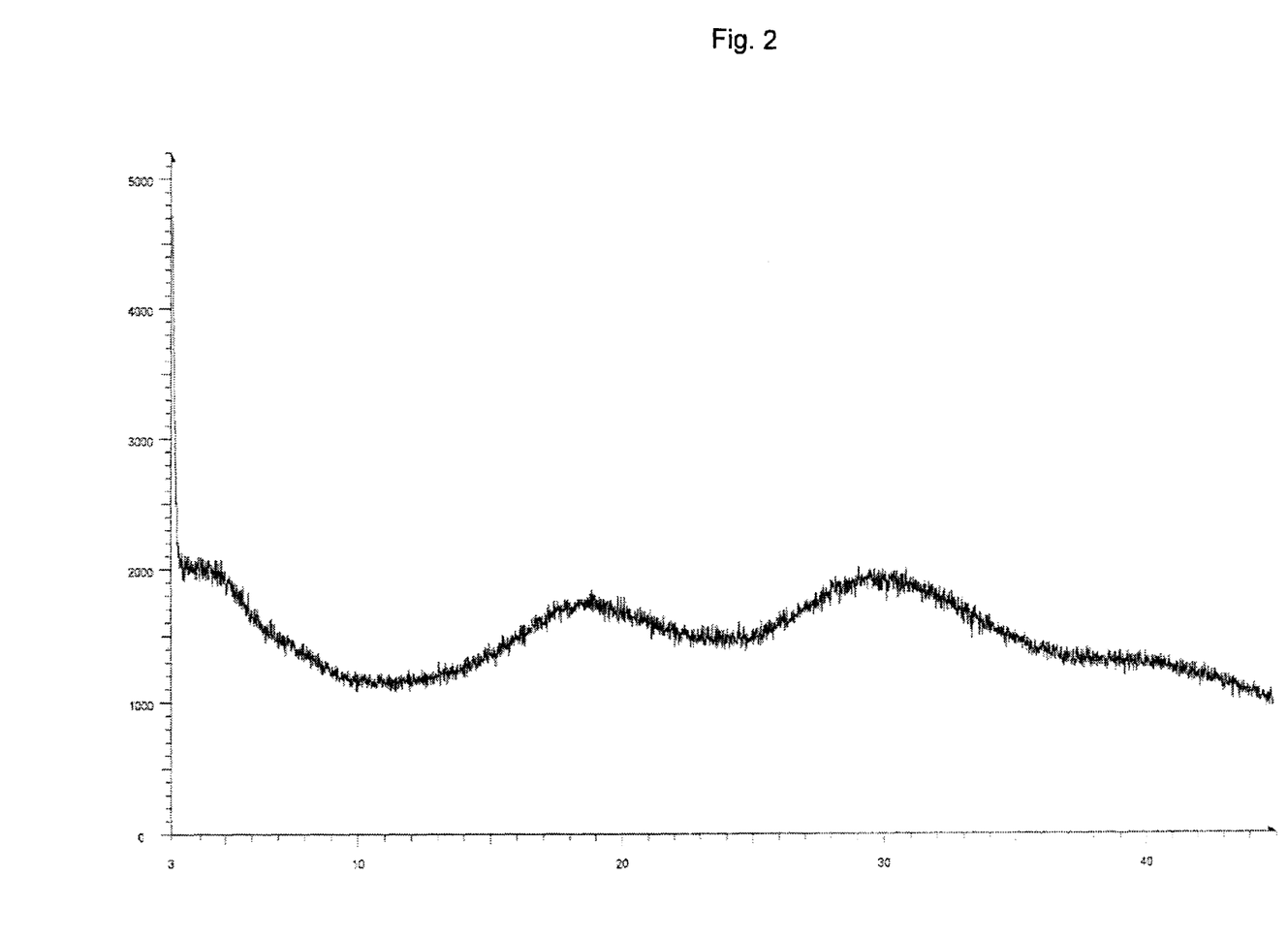
FIG. 2 is an XRPD pattern of a product prepared according to Example 10, after storage for 50 days at 2-8° C.

The lyophilized product thus obtained is found to be amorphous in nature as is evidenced by the XRPD pattern depicted in FIG. 1. After storage for 50 days at 2-8° C., the lyophilized product is found to retain its amorphous nature as shown in the XRPD pattern depicted in FIG. 2. In the drawings, the y-axis is intensity units and the x-axis is the 2-theta angle, in degrees. XRPD patterns depicted herein are obtained using copper Ka radiation.

While particular embodiments have been illustrated and described, it will be apparent to those skilled in the art that various other changes and modifications can be made without departing from the spirit and scope of the disclosure. It is therefore intended to cover all such changes and modifications that are within the scope of this application.

ADDITIONAL DISCLOSURE

Embodiments of the application further include the following:

A. Compositions of epothilone compounds prepared by using tertiary-butyl alcohol in combination with other non-aqueous organic solvents which are lyophilisable, and processes of lyophilization.

B. Compositions of epothilone compounds prepared using mixtures of acetone and tertiary-butyl alcohol, and processes of lyophilization.

C. Compositions of epothilone compounds prepared using mixtures of acetonitrile and tertiary-butyl alcohol, and processes of lyophilization.

D. Processes for preparing compositions of epothilone compounds having significantly lower amounts of drug-related impurities than the marketed Ixempra® preparation, involving the use of a mixture of tertiary-butyl alcohol and another non-aqueous organic solvent, and processes of lyophilization.

E. Pharmaceutical formulations of epothilone compounds having significantly lower amounts of total drug-related impurities than the currently marketed IXEMPRA preparation, following storage at 40° C. and 75% RH.

We claim:

1. A process for preparing a formulation of an epothilone compound having formula A, where R is hydrogen, or an alkyl, substituted alkyl, aryl, substituted aryl, or heterocyclic group, including any salts and any stereoisomers of the compounds or salts, comprising:
  a) dissolving the epothilone compound in a mixture of at least 20% by volume tertiary-butanol and acetone or acetonitrile;
  b) drying the solution at about −80° C. to about 40° C. under vacuum from about 5 millitorr to about 250 millitorr, to form a primary lyophilized product; and
  c) drying the primary lyophilized product at about 10° C. to about 30° C. under vacuum from about 5 millitorr to about 300 millitorr, to provide a lyophilized product of the epothilone compound.

2. The process of claim 1, wherein an epothilone compound has formula III,

3. The process of claim 1, wherein the epothilone compound is dissolved in a mixture of at least 20% tertiary-butanol and acetone or acetonitrile.

4. The process of claim 1 wherein said drying in step b) is carried out at about −60° C. to about 30° C. and under vacuum from about 5 millitorr to about 250 millitorr.

5. The process of claim 1 wherein drying in step c) is carried out at about 20° C. to about 30° C. and under vacuum from about 200 millitorr to about 300 millitorr.

6. The process of claim 1, further comprising: d) packaging the lyophilized product in a first vial and packaging in a second vial a sufficient quantity of a mixture comprising at least one nonionic surfactant and at least one alcohol to permit reconstitution of the lyophilized product.

7. The process of claim 6, wherein the mixture of d) comprises approximately equal parts by volume of alcohol USP and at least one nonionic surfactant comprising a polyethoxylated castor oil.

8. A pharmaceutical product prepared according to claim 7.

9. The pharmaceutical product of claim 8, wherein a second vial comprises approximately equal volume amounts of at least one nonionic surfactant and alcohol USP.

10. A process for preparing a formulation of ixabepilone, comprising:
  a) dissolving ixabepilone in a mixture of at least 20% by volume tertiary-butanol and acetone or acetonitrile;
  b) drying the solution at about −80° C. to about 40° C. under vacuum from about 5 millitorr to about 250 millitorr, to form a primary lyophilized product; and
  c) drying the primary lyophilized product at about 10° C. to about 30° C. under vacuum from about 5 millitorr to about 300 millitorr, to provide a lyophilized product.

11. The process of claim 10, further comprising: d) packaging the lyophilized product in a first vial and packaging in a second vial a sufficient quantity of a mixture comprising at least one nonionic surfactant and at least one alcohol to permit reconstitution of the lyophilized product.

12. The process of claim 11, wherein the mixture of d) comprises approximately equal parts by volume of alcohol USP and at least one nonionic surfactant comprising a polyethoxylated castor oil.

13. A pharmaceutical product prepared according to claim 11.

14. The pharmaceutical product of claim 13, wherein a second vial comprises approximately equal volume amounts of at least one nonionic surfactant and alcohol USP.

* * * * *